(12) United States Patent
An et al.

(10) Patent No.: US 12,315,355 B1
(45) Date of Patent: May 27, 2025

(54) CHEMICAL MATERIAL LEAKAGE ALARM-PROVIDING SYSTEM AND CHEMICAL MATERIAL LEAKAGE ALARM-PROVIDING METHOD

(71) Applicant: Republic of Korea (National Disaster Management Research Institute), Ulsan (KR)

(72) Inventors: Su Bin An, Ulsan (KR); Kyung Su Lee, Ulsan (KR); Hyun Seung Lee, Ulsan (KR); Joo Yeon Oh, Ulsan (KR); Gun Sik Jeong, Ulsan (KR); Won Kyu Oh, Ulsan (KR); Sung Geun Bae, Ulsan (KR)

(73) Assignee: Republic of Korea (National Disaster Management Research Institute), Ulsan (KR)

( * ) Notice: Subject to any disclaimer, the term of this patent is extended or adjusted under 35 U.S.C. 154(b) by 0 days.

(21) Appl. No.: 18/870,277

(22) PCT Filed: Jul. 6, 2023

(86) PCT No.: PCT/KR2023/009568
§ 371 (c)(1),
(2) Date: Nov. 27, 2024

(87) PCT Pub. No.: WO2024/010391
PCT Pub. Date: Jan. 11, 2024

(30) Foreign Application Priority Data

Jul. 6, 2022 (KR) .................. 10-2022-0083014

(51) Int. Cl.
*G01N 33/00* (2006.01)
*G06V 20/52* (2022.01)
(Continued)

(52) U.S. Cl.
CPC ............. *G08B 21/12* (2013.01); *G06V 20/52* (2022.01); *G08B 31/00* (2013.01)

(58) Field of Classification Search
CPC .......... G08B 21/12; G08B 31/00; G06V 20/52
See application file for complete search history.

(56) References Cited

U.S. PATENT DOCUMENTS

2009/0271125 A1* 10/2009 Vergassola ........... G05D 1/0274
702/22
2017/0032632 A1* 2/2017 Joseph .................... H04W 4/90
(Continued)

FOREIGN PATENT DOCUMENTS

KR 10-2123568 B1 6/2020
KR 10-2021-0058081 A 5/2021
(Continued)

*Primary Examiner* — An T Nguyen
(74) *Attorney, Agent, or Firm* — Bridgeway IP Law Group, PLLC; Sang Ho Lee; Hyun Woo Shin

(57) ABSTRACT

Provided is a chemical material leakage alarm-providing method of detecting chemical material leakage in a monitoring area and providing a user alert, the method including the steps of: sensing external environmental information using an environmental information-collecting sensor; obtaining data about a chemical material using a chemical material-detecting device; predicting a diffusion pattern of the chemical material based on the environmental information; detecting chemical material information based on the chemical material data; and providing a user alert based on at least one of the diffusion pattern of the chemical material and the chemical material information.

15 Claims, 15 Drawing Sheets

(51) Int. Cl.
　　　*G08B 21/12*　　　(2006.01)
　　　*G08B 31/00*　　　(2006.01)

(56) References Cited

U.S. PATENT DOCUMENTS

| | | | | |
|---|---|---|---|---|
| 2019/0158789 | A1* | 5/2019 | Snyder | G06V 20/52 |
| 2020/0100115 | A1* | 3/2020 | Skaaksrud | G01K 3/005 |
| 2021/0404905 | A1* | 12/2021 | Cho | G06F 3/14 |
| 2022/0205967 | A1* | 6/2022 | Thoma | H04Q 9/00 |

FOREIGN PATENT DOCUMENTS

| | | |
|---|---|---|
| KR | 10-2022-0038584 A | 3/2022 |
| KR | 10-2022-0083872 A | 6/2022 |
| KR | 10-2540986 B1 | 6/2023 |

\* cited by examiner

CHEMICAL MATERIAL LEAKAGE ALARM-PROVIDING SYSTEM AND CHEMICAL MATERIAL LEAKAGE ALARM-PROVIDING METHOD

TECHNICAL FIELD

The present invention relates to a chemical material leakage alarm-providing system and a chemical material leakage alarm-providing method.

BACKGROUND ART

The core processes of cutting-edge industries such as semiconductors and displays inevitably use various hazardous gases including fluorine-based, chlorine-based, bromine-based, and nitric acid-based acid gases, and basic gases such as ammonia and amines.

Recently, chemical accidents such as high-concentration leaks of hazardous gases or hazardous chemical materials have frequently occurred in various types of industrial sites.

Due to the problems caused by the leakage of such hazardous chemical materials, the Environmental Conservation Act, etc., requires the self-measurement of various environmental pollutants or self-measurement thereof by an agency, and in some cases, it is needed to measure environmental pollutants in real time on site.

However, the damage caused by chemical accidents is increasing because the occurrence of chemical accidents is not recognized or transmitted. In addition, there is a problem that chemical accidents cannot be responded to quickly due to insufficiency of information related to chemical accidents or improper delivery of the information.

To minimize the damage caused by chemical material leakage and enable a quick response, research into an alarm system capable of, when chemical materials harmful to the human body are leaked at industrial sites or the leakage of chemical materials exceeds the standard, notifying these situations the surroundings is needed. Accordingly, it may be difficult to monitor the diffusion pattern of leaked chemical materials in real-time.

DISCLOSURE

Technical Problem

Therefore, the present invention has been made in view of the above problems, and it is one object of the present invention to provide a chemical material leakage alarm apparatus and a chemical material leakage alarm-providing method.

It is another object of the present invention to provide a chemical material leakage alarm apparatus configured to provide a user alert based on at least one of the diffusion pattern of a chemical material and chemical material information, and a chemical material leakage alarm-providing method.

Technical Solution

In accordance with an aspect of the present invention, the above and other objects can be accomplished by the provision of a chemical material leakage alarm-providing method of detecting chemical material leakage in a monitoring area and providing a user alert, the chemical material leakage alarm-providing method including: sensing external environmental information using an environmental information-collecting sensor; obtaining data about a chemical material using a chemical material-detecting device; predicting a diffusion pattern of the chemical material based on the environmental information; detecting chemical material information based on the chemical material data; and providing a user alert based on at least one of the diffusion pattern of the chemical material and the chemical material information.

In another aspect, in the providing, a user alert may be provided to correspond to a leakage state determined according to at least one of the diffusion pattern of the chemical material and the chemical material information, and may include at least one of an alarm sound, an alarm light and an alarm vibration.

In another aspect, in the detecting, chemical material information including at least one of a type and concentration of the chemical material may be detected.

In another aspect, in the providing, a first user alert may be provided when the detected chemical material is not included in a preset leakage-allowed chemical material list.

In another aspect, in the providing a user alert, a second user alert different from the first user alert may be provided when a diffusion pattern range of the chemical material not included in the leakage-allowed chemical material list exceeds a preset reference diffusion pattern range.

In another aspect, the first user alert may include at least one of an alarm sound of a first pattern and an alarm light of a first color, and the second user alert may include at least one of an alarm sound of a second pattern different from the first pattern and an alarm light of a second color different from the first color.

In another aspect, the diffusion pattern range may include at least one of a diffusion speed and diffusion range of a chemical material.

In accordance with another aspect of the present invention, provided is a chemical material leakage alarm-providing system installed at a location spaced apart from a monitoring area where a chemical material is leaked and configured to detect leakage of the chemical material and provide the leakage to a user alert, the chemical material leakage alarm-providing system including: a chemical material-detecting device for obtaining data of the chemical material leaking from the monitoring area; an environmental information-collecting sensor for sensing external environmental information; a controller including a memory storing one or more programs including a command; and a processor executing the programs to predict a diffusion pattern of the chemical material based on the environmental information, detect chemical material information based on data about the chemical material, and generate an alarm control signal based on at least one of the diffusion pattern of the chemical material and the chemical material information; and an alarm device for providing a user alert corresponding to the alarm control signal transmitted from the controller.

In another aspect, the user alert may correspond to a leakage state determined according to at least one of the diffusion pattern of the chemical material and the chemical material information, and may include at least one of an alarm sound, an alarm light and an alarm vibration.

In another aspect, the chemical material information may include at least one of a type and concentration of the chemical material.

In another aspect, the processor may determine whether the detected chemical material is included in a leakage-allowed chemical material list stored in the memory, and, when the detected chemical material is not included in the leakage-allowed chemical material list, may generate a first alarm control signal such that the alarm device provides a first user alert, and transmit it to the alarm device.

In another aspect, when a diffusion pattern range of the chemical material not included in the leakage-allowed chemical material list is outside a reference diffusion pattern range stored in the memory, the processor may generate a second alarm control signal such that the alarm device provides a second user alert different from the first user alert, and transmits it to the alarm device.

In another aspect, the first user alert may include at least one of an alarm sound of a first pattern and an alarm light of a first color, and the second user alert may include at least one of an alarm sound of a second pattern different from the first pattern and an alarm light of a second color different from the first color.

In another aspect, the diffusion pattern range may include at least one of a diffusion speed and diffusion range of a chemical material.

In another aspect, the chemical material leakage alarm-providing system may further include an image camera for photographing an external object.

In another aspect, the processor may specify a leakage area of the chemical material by analyzing an image of the monitoring area photographed by the image camera, and control a position of the chemical material-detecting device such that the chemical material-detecting device faces the specified leakage area of the chemical material.

In another aspect, the processor may specify a plurality of target detection areas based on three-dimensional space modeling data for the monitoring area, and determine a position of the image camera such that two target detection areas among the plural target detection areas are photographed without overlapping each other.

Advantageous Effects

According to various embodiments of the present invention, a chemical material leakage alarm apparatus and a chemical material leakage alarm-providing method can be provided.

In addition, according to various embodiments of the present invention, a chemical material leakage alarm apparatus and chemical material leakage alarm-providing method that provide a user alert based on at least one of the diffusion pattern of a chemical material and chemical material information can be provided.

In addition, according to various embodiments of the present invention, a chemical material leakage alarm apparatus and chemical material leakage alarm-providing method that provide various types of user alarms based on environmental information, such as wind direction, wind speed and temperature, collected by an environmental information-collecting sensor and chemical material information, such as the type and concentration, on the chemical material detected by a chemical material-detecting device can be provided.

In addition, a quick alarm to notify of a leak of hazardous chemical materials in industrial sites can be provided by using the chemical material leakage alarm apparatus and chemical material leakage alarm-providing method according to various embodiments of the present invention, so that human casualties caused by chemical material leakage can be minimized.

In addition, the chemical material leakage alarm apparatus and chemical material leakage alarm-providing method according to various embodiments of the present invention can provide more accurate alarms by using chemical material data acquired based on an image in which a plurality of target detection areas do not overlap each other.

In addition, the chemical material leakage alarm apparatus and chemical material leakage alarm-providing method according to various embodiments of the present invention, can provide more accurate alarms by correcting a first diffusion pattern prediction result of a chemical material in a first target detection area based on a second diffusion pattern of a chemical material in a second target detection area adjacent to the first target detection area.

BEST MODE

Figure 1:
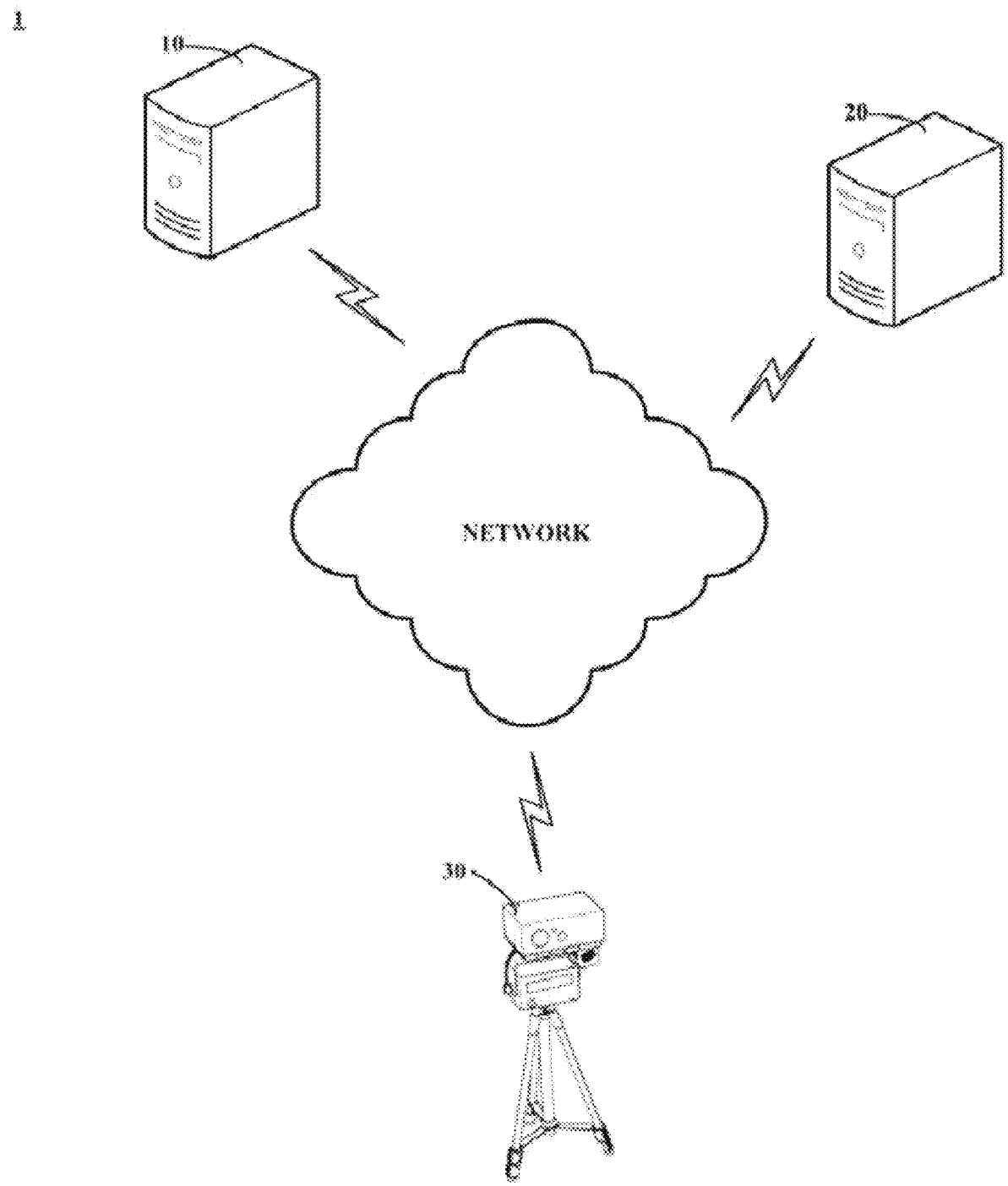
FIG. 1 is a simplified diagram illustrating an exemplary configuration of a chemical material leakage-monitoring system according to an embodiment.

As the invention allows for various changes and numerous embodiments, particular embodiments are illustrated in the drawings and described in detail in the written description. The attached drawings for illustrating exemplary embodiments of the present invention are referred to in order to clearly explain the effects and characteristics of the present invention and a method of accomplishing the present invention. The scope of the present invention is not limited to the following embodiments and can be embodied in various forms. In the embodiments below, the terms "first," "second," etc. are not used in a restrictive sense, but are used to distinguish one component from another component. Also, singular expressions include plural expressions unless the context clearly indicates otherwise. It will be further understood that the terms "comprises" or "has" refer to the presence of features or constructions described herein, but do not preclude the possibility of one or more features or constructions to be added. For convenience of explanation, components in the drawings may be exaggerated or reduced in size. For example, the size and thickness of each component shown in the drawings are arbitrarily shown for convenience of explanation, so the present invention is not necessarily limited to what is shown.

Hereinafter, embodiments of the present invention are described in detail with reference to the accompanying drawings. When describing with reference to the drawings, identical or corresponding components are given the same drawing reference numerals and redundant descriptions thereof will be omitted.

Chemical Material Leakage-Monitoring System

FIG. 1 is a simplified diagram illustrating an exemplary configuration of a chemical material leakage-monitoring system 1 according to an embodiment.

Referring to FIG. 1, the chemical material leakage-monitoring system 1 according to an embodiment may include a central server 10 configured to manage a chemical material leakage-monitoring process, a computing device 20 configured to perform calculations necessary for providing a chemical material leakage alarm and a chemical material leakage alarm-providing system 30 capable of detecting chemical material and providing a chemical material leakage alarm. The central server 10, the computing device 20 and the chemical material leakage alarm-providing system 30 may communicate with each other through a network.

In detail, the network refers to a connection structure that enables information exchange between respective nodes, such as the central server 10, the computing device 20, and the chemical material leakage alarm-providing system 30. Examples of this network include, but are not limited to, a 3rd Generation Partnership Project (3GPP) network, a Long Term Evolution (LTE) network, a World Interoperability for Microwave Access (WIMAX) network, the Internet, a Local Area Network (LAN), a Wireless Local Area Network (Wireless LAN), a Wide Area Network (WAN), a Personal Area Network (PAN), a Bluetooth network, a satellite broadcasting network, an analog broadcasting network, a Digital Multimedia Broadcasting (DMB) network, and the like.

In addition, the chemical material leakage-monitoring system 1 may further include at least one fixed sensor (not shown) and at least one fixed camera (not shown).

The fixed sensor may include at least one of a wind direction sensor, wind speed sensor, and temperature sensor installed around a monitoring target (e.g., a chemical material treatment device, a chemical material treatment plant, etc.). However, the present invention is not limited thereto, and the fixed sensor may include various types of sensors other than the listed examples.

The fixed camera may include at least one of a thermal imaging camera, RGB camera, and depth camera installed around a monitoring target. However, the present invention is not limited thereto, and the fixed camera may include various types of cameras other than the listed examples.

The central server 10 may process data related to various physical parameters and images of the monitoring target collected by the fixed sensor, fixed camera, and chemical material leakage alarm-providing system 30 installed around the monitoring target, and may produce information about an expected leakage point where the chemical material is expected to leak, and store the information. However, the present invention is not limited thereto, and a separate computing device 20 or the chemical material leakage alarm-providing system 30 may directly process various physical parameters and image-related data for the monitoring target to perform a chemical material leakage-monitoring process.

For example, the central server 10 or the computing device 20 may detect whether a chemical material has leaked, based on an image (thermal image or RGB image) of the surroundings of the monitoring target acquired by the fixed camera. In this case, the central server 10 or the computing device 20 may detect whether a chemical material has leaked, using a deep learning method based on an image of the surroundings of the monitoring target.

In addition, the central server 10 or the computing device 20 may calculate the diffusion pattern of the leaked chemical material based on data about wind direction, wind speed, and temperature and images of the surroundings of the monitoring target, and may generate data about the initial expected leak point of the chemical material by tracing back this diffusion pattern. Data on the initial expected leak point generated by the central server 10 or the computing device 20 may be transmitted to the chemical material leakage alarm-providing system 30 via a network.

The chemical material leakage alarm-providing system 30 may provide various user alerts to the user based on various data from the central server 10 or the computing device 20, or based on at least one of the environmental information, such as wind direction, wind speed, temperature, etc., and chemical material information, sensed by itself.

A method of providing various user alerts according to various leakage conditions by the chemical material leakage alarm-providing system 30 is described below with reference to FIGS. 5 to 15.

Chemical Material Leakage Alarm-Providing System

Figure 2:
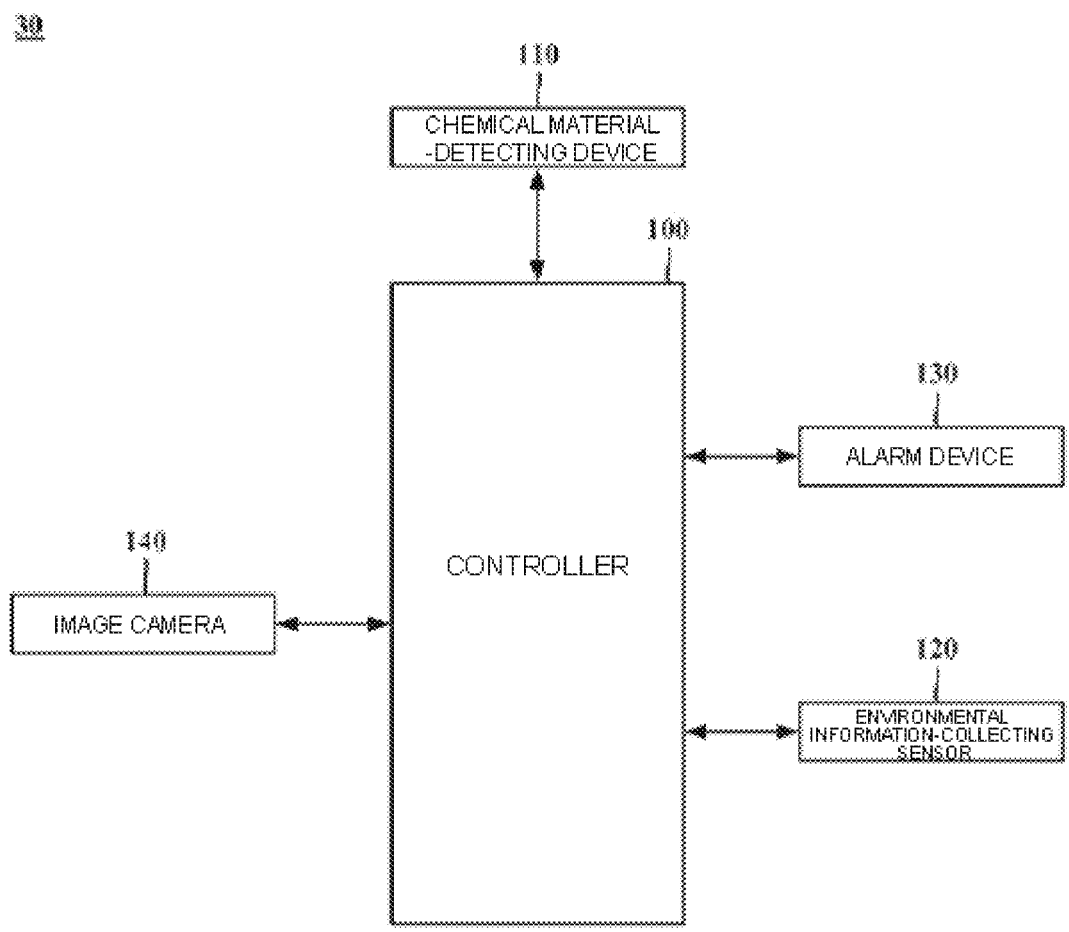
FIG. 2 illustrates a block diagram of a chemical material leakage alarm-providing system according to an embodiment.
Figure 3:
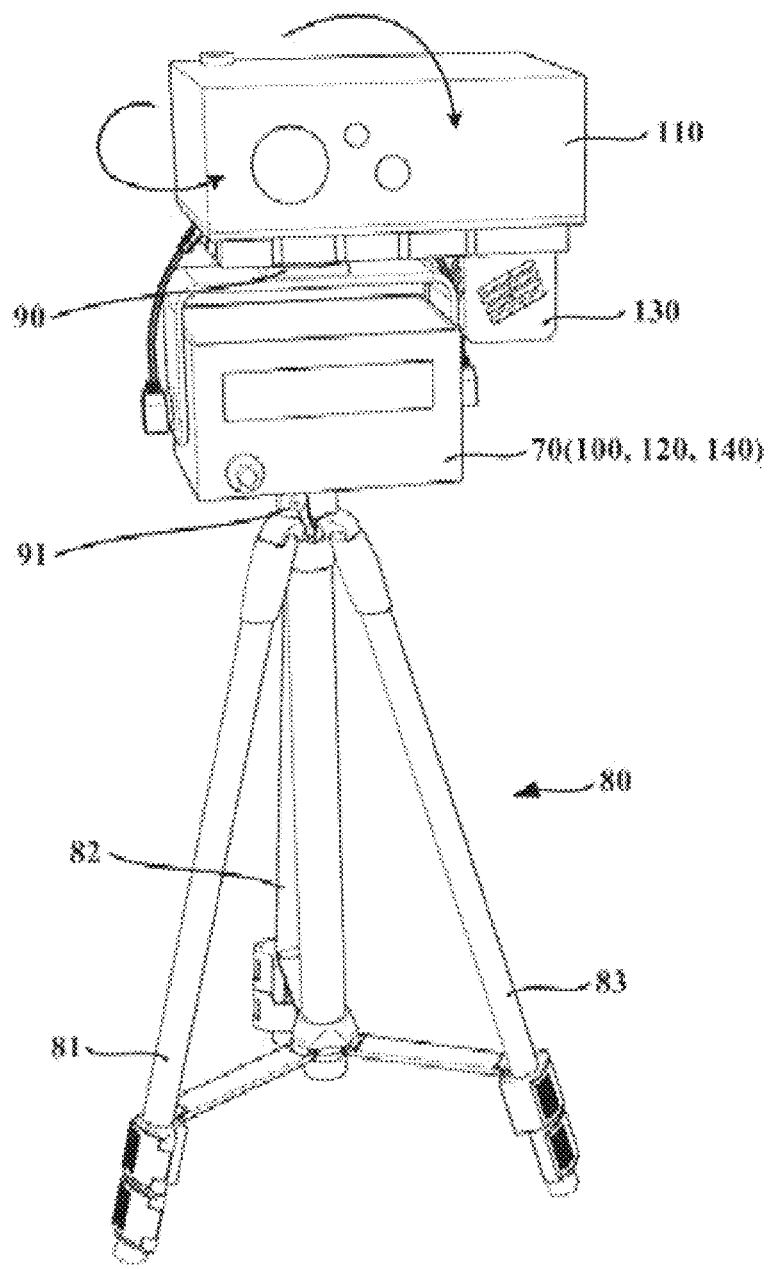
FIG. 3 illustrates an exemplary configuration of the chemical material leakage alarm-providing system according to an embodiment.
Figure 4:
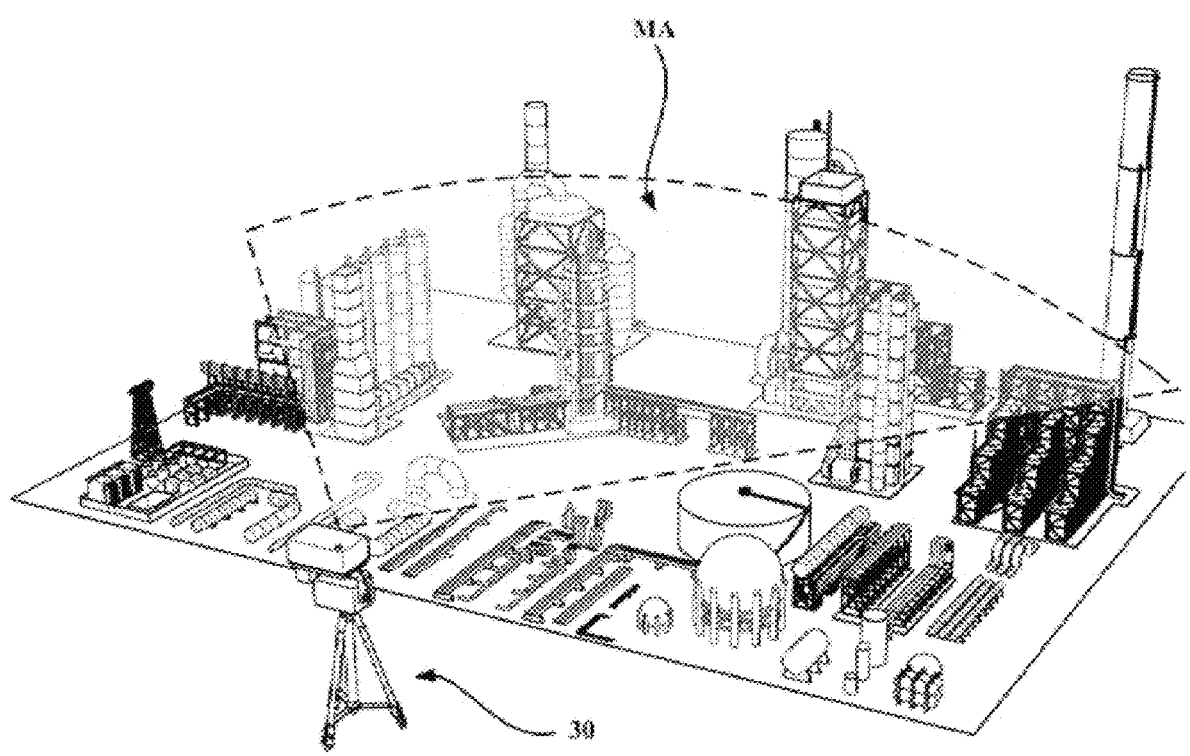
FIG. 4 is a drawing explaining a monitoring area of the chemical material leakage alarm-providing system.
Figure 5:
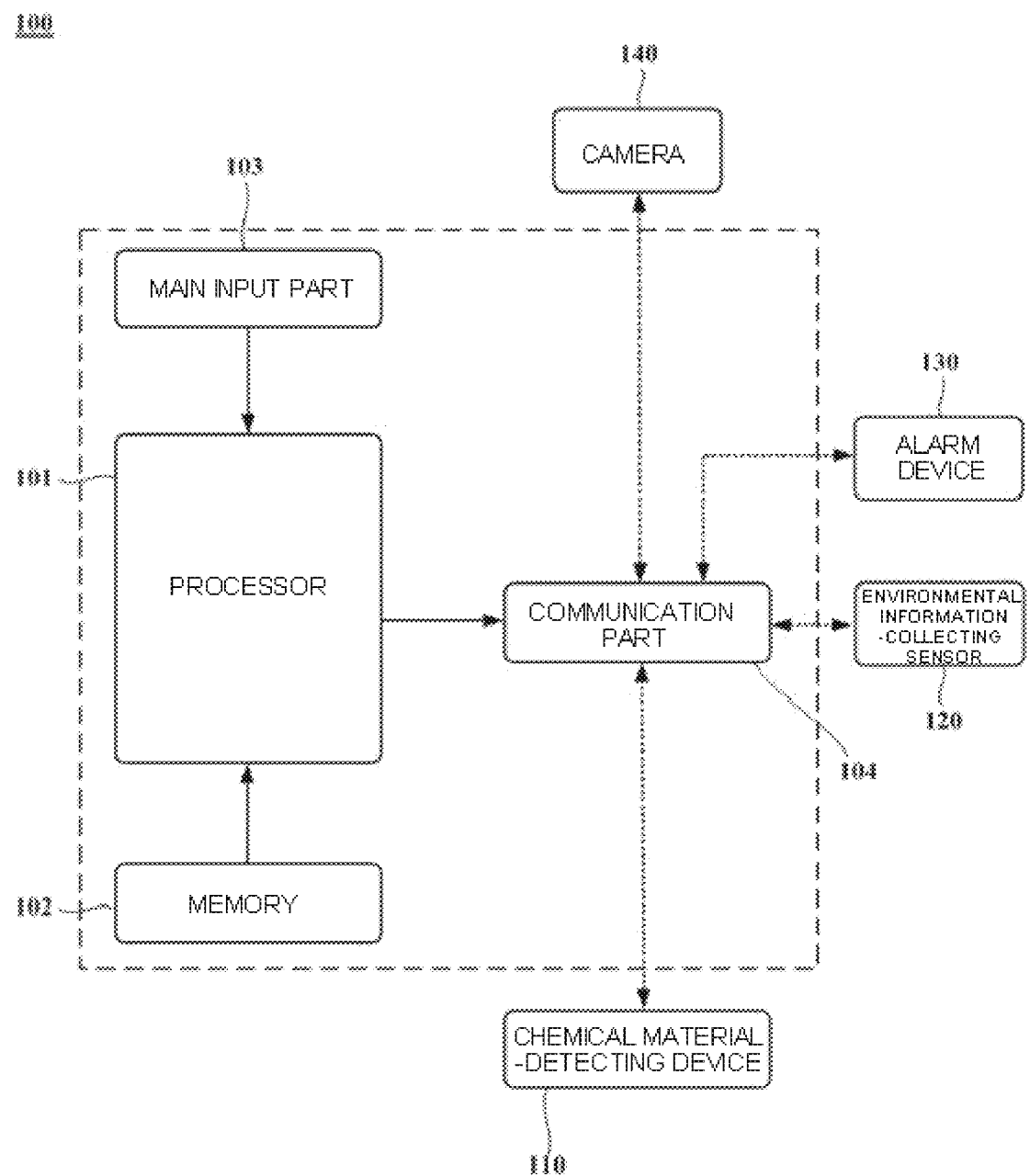
FIG. 5 illustrates a block diagram of a controller.

FIG. 2 illustrates a block diagram of a chemical material leakage alarm-providing system 30 according to an embodiment. FIG. 3 illustrates an exemplary configuration of the chemical material leakage alarm-providing system 30 according to an embodiment. FIG. 4 illustrates a monitoring area MA of the chemical material leakage alarm-providing system 30. FIG. 4 illustrates a monitoring area of a chemical material leakage alarm-providing system. FIG. 5 illustrates a block diagram of a controller 100.

Referring to FIG. 2, the chemical material leakage alarm-providing system 30 according to an embodiment may include a controller 100, a chemical material-detecting device 110, an environmental information-collecting sensor 120 and an alarm device 130.

The controller 100 may generate various alarm control signals based on various data sensed by the chemical material-detecting device 110 and the environmental information-collecting sensor 120.

The alarm device 130 may provide various user alerts to a user according to the alarm control signals transmitted from the controller 100.

In addition, the chemical material leakage alarm-providing system 30 may further include an image camera 140 that photographs an external object.

The controller 100 may control the operations of the chemical material-detecting device 110, the environmental information-collecting sensor 120, the alarm device 130, and the image camera 140. In detail, the controller 100 may control the chemical material-detecting device 110 and the environmental information-collecting sensor 120 so that chemical material information can be detected and environmental information can be sensed.

In addition, the controller 100 may control the position of the chemical material-detecting device 110 and the environmental information-collecting sensor 120.

In addition, the controller 100 may generate an alarm control signal for controlling the alarm device 130 based on at least one of chemical material information and environmental information.

the chemical material-detecting device 110 may detect fine chemical materials in solid, liquid, and gaseous states from a distance. In detail, The chemical material-detecting device 110 may detect the type and concentration of solid, liquid, and gaseous chemical materials spread in the air.

For example, the chemical material-detecting device 110 may detect fine chemical materials in solid, liquid, and gaseous states from a distance using an analysis device applied with an FT-IR method. In addition, the chemical material-detecting device 110 may further include a thermal imaging camera, and may detect the characteristics of the chemical material based on the image captured by the thermal imaging camera.

However, the present invention is not limited thereto, and the chemical material-detecting device 110 may detect a chemical material from a distance using various types of devices other than the analysis device applied with an FT-IR method and the thermal imaging camera.

The chemical material information detected by the chemical material-detecting device 110 may be used to generate an alarm control signal for controlling the alarm device 130.

the environmental information-collecting sensor 120 may include at least one of a wind speed sensor, a wind direction sensor and a temperature sensor.

The environmental information-collecting sensor 120 may sense the surrounding environment information, such as wind speed, wind direction, and temperature, of a surrounding environment. The surrounding environment information sensed by an environmental information-collecting sensor 120 may be used to predict the diffusion patterns of a leaked chemical material.

The alarm device 130 may provide a user alert including at least one of an alarm sound, an alarm light and an alarm vibration according to an alarm control signal transmitted from the controller 100. For example, the alarm device 130 may include at least one of a speaker, a lighting device, and a vibration device.

The various leakage states of the chemical material may be determined according to at least one of the diffusion patterns of the chemical material predicted based on the chemical material information detected by the chemical material-detecting device 110 and the surrounding environment information sensed by the environmental information-collecting sensor 120. The alarm device 130 may provide various forms of user alerts corresponding to various leakage states.

For example, the alarm device 130 may provide a first user alert corresponding to a first leakage state of a chemical material, may provide a second user alert corresponding to a second leakage state different from the first leakage stat, and a third user alert corresponding to a third leakage state different from the first leakage state and the second leakage state.

Here, the first user alert, the second user alert and the third user alert may be implemented in different forms. For example, the first user alert may include an alarm sound of a first pattern, the second user alert may include an alarm sound of a second pattern and an alarm light of a first color, and the third user alert may include an alarm sound of a third pattern and an alarm light of a second color.

Since the alarm device 130 provides different user alerts according to the leakage status of different chemical materials in such manners, a user may quickly recognize various situations and take appropriate countermeasures accordingly, thereby preventing the expansion of accidents caused by chemical materials harmful to the human body.

The image camera 140 may capture an image of an external object. The image camera 140 may include at least one of a thermal imaging camera and an RGB camera.

The image camera 140 may obtain image information on a sensing target by detecting an optical signal that is output from a light source and is reflected by the sensing target. In this specification, the image camera 140 may include a light source, a pixel array and a light detection circuit. The light source may include a plurality of light-emitting elements (e.g., Vertical Cavity Surface Emitting Lasers (VCSELs), LEDs, etc.) that output light signals of a specific band wavelength. The pixel array may include a plurality of pixels. Here, each pixel may include a plurality of light-sensitive elements (e.g., photodiodes, etc.) and a color filter (e.g., RGB filter).

In addition, the image camera 140 may include a depth camera. The depth camera may be referred to as a distance sensor. For example, as the distance sensor, a lidar device may be used.

The image camera 140 may have a single camera structure including at least one of a thermal imaging camera and an RGB camera and a depth camera. In this case, there is an advantage in that a compact form factor for the image camera 140 may be achieved.

An image captured by the image camera 140 may be used to detect chemical material leakage. In detail, the image captured in real-time by the image camera 140 may be analyzed to determine whether a chemical material has leaked.

Referring to FIG. 3, the chemical material leakage alarm-providing system 30 according to an embodiment may include a main housing 70 inside which the controller 100, the environmental information-collecting sensor 120 and the image camera 140 are provided.

The main housing 70 may include an internal space in which the controller 100, the environmental information-collecting sensor 120 and the image camera 140 are provided, and may prevent the controller 100, the environmental information-collecting sensor 120 and the image camera 140 from being damaged by external impact. In this case, a sensing part of the environmental information-collecting sensor 120 and a lens part of the image camera 140 may be configured to be exposed to the outside of the main housing 70.

However, the present invention is not limited thereto, and the environmental information-collecting sensor 120 and the image camera 140 may be provided outside the main housing 70.

A fixing frame 80 may be provided at a lower part of the main housing 70. The fixing frame 80 may be configured to be fixed at a location where the chemical material leakage alarm-providing system 30 is installed.

For example, the fixing frame 80 may be implemented in a tripod shape including a first leg 81, a second leg 82 and a third leg 83. However, the present invention is not limited thereto, and the fixing frame 80 may be implemented in various shapes other than a tripod shape.

The chemical material-detecting device 110 may be provided the main housing 70. A first tilting part 90 may be provided between the main housing 70 and the chemical material-detecting device 110.

The chemical material-detecting device 110 may be connected to the main housing 70 through the first tilting part 90, and the position of the chemical material-detecting device 110 may be changed by controlling the operation of the first tilting part 90. For example, the chemical material-detecting device 110 may rotate up, down, left, and right according to the operation of the first tilting part 90.

Meanwhile, a second tilting part 91 may be provided between the fixing frame 80 and the main housing 70. The main housing 70 may be connected to the fixing frame 80 through the second tilting part 91, and the position of the main housing 70 may be changed by controlling the operation of the second tilting part 91. For example, the main housing 70 may rotate up, down, left, and right according to the operation of the second tilting part 91.

The alarm device 130 may be connected to the chemical material-detecting device 110. For example, the alarm device 130 may be provided under the chemical material-detecting device 110.

However, the present invention is not limited thereto, and the alarm device 130 may be spaced apart from the chemical material-detecting device 110 without being connected thereto. For example, the alarm device 130 may be provided inside or outside the main housing 70.

Referring to FIG. 4, the chemical material leakage alarm-providing system 30 may be fixed at a specific point, and may observe a monitoring area MA spaced apart by a certain distance.

For example, the chemical material leakage alarm-providing system 30 may capture images of the monitoring area MA in real-time using the image camera 140, and detect chemical material information on the monitoring area MA using the chemical material-detecting device 110. Here, the monitoring area MA may be various types of industrial sites, such as semiconductor factories, where chemical materials may leak.

FIG. 3 illustrates a block diagram of the controller 100.

Referring to FIG. 3, the controller 100 may include a processor 101, a memory 102, a main input part 103 and a communication part 104. In addition, the controller 100 may further include a main input part 103 connected to the processor 101.

In the memory 102, one or more programs including a command may be stored. One or more programs may be executed by the processor 101.

The processor 101 may perform a preset operation based on an input signal that is input from the main input part 103. The main input part 103 may be installed on the main housing 70. In addition, the main input part 103 may be a button-type or dial-type input device, but is not limited thereto. The power of the controller 100 may be turned on/off by the main input part 103.

The communication part 104 may communicate with the processor 101, the chemical material-detecting device 110, the environmental information-collecting sensor 120, the alarm device 130, and the image camera 140 using methods such as Bluetooth, infrared communication, RFID, WLAN, and Wibro. For example, chemical material data obtained by the chemical material-detecting device 110, environmental information data sensed by the environmental information-collecting sensor 120, and image data captured by the image camera 140 may be transmitted to the communication part 104.

In addition, the communication part 104 may communicate with an external device to transmit and receive data. For example, the communication part 104 may communicate with the central server 10 and the computing device 20.

The processor 101 may generate an alarm control signal based on various data received from the chemical material-detecting device 110, the environmental information-collecting sensor 120, and the image camera 140 by executing a program stored in a memory. The method by which the processor 201 generates an alarm control signal and, accordingly, the alarm device 130 provides a user alert is described below with reference to FIGS. 6 to 15.

Chemical Material Leakage Alarm-Providing Method.

Figure 6:
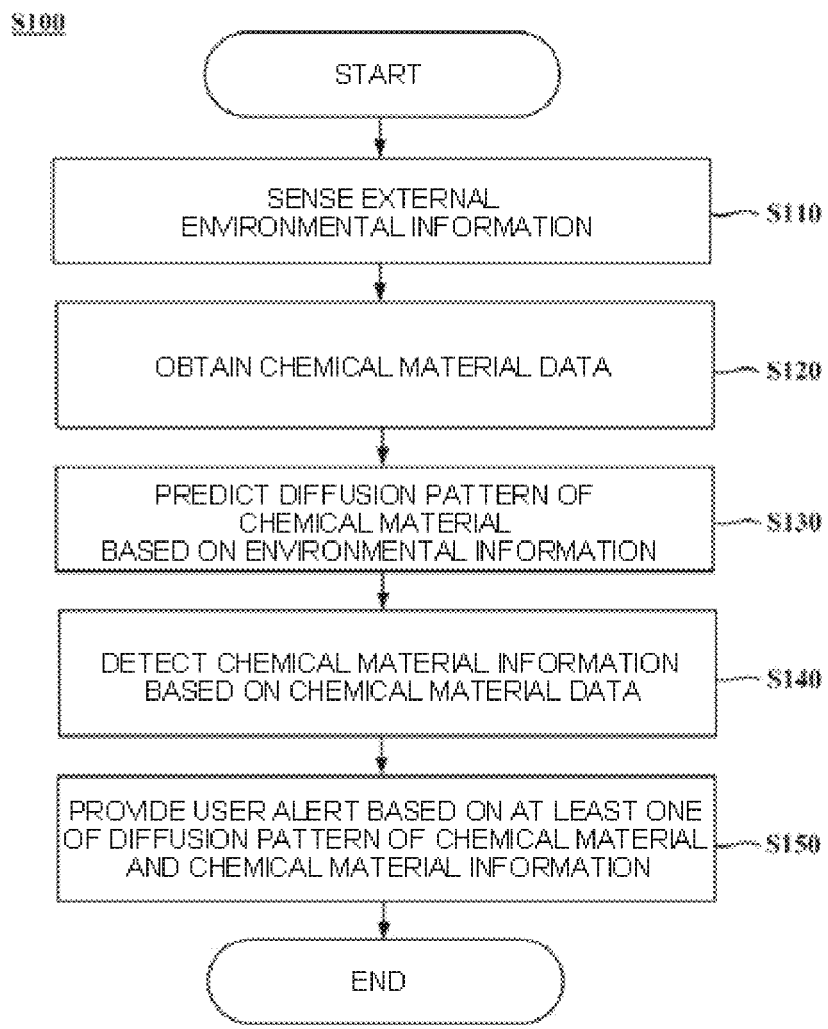
FIG. 6 illustrates a flowchart of a chemical material leakage alarm-providing method according to an embodiment.
Figure 7:
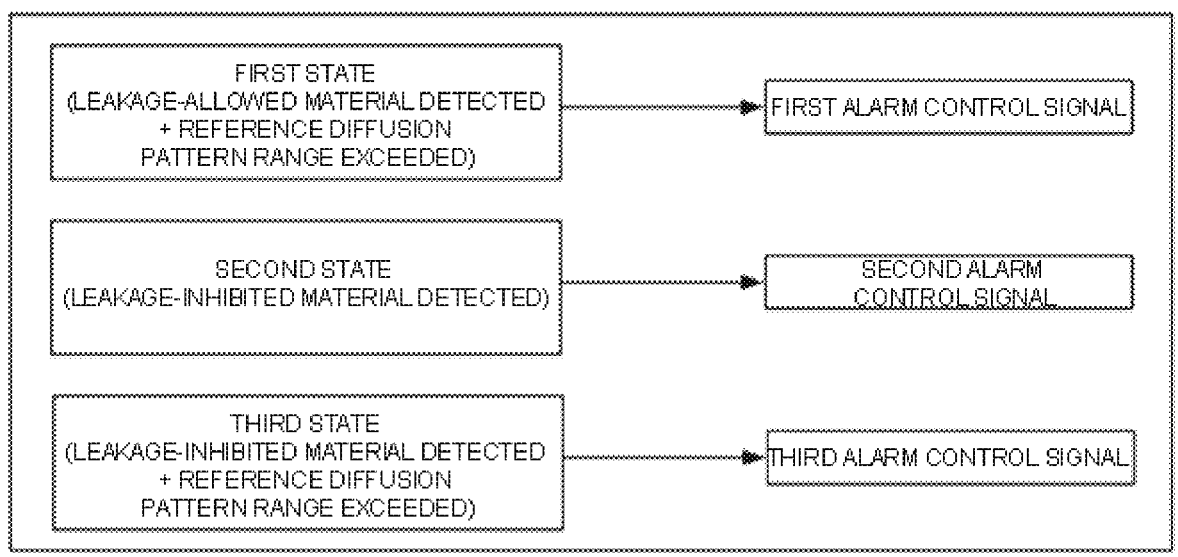
FIG. 7 illustrates an alarm data set in which various chemical material leakage states stored in the memory are matched with various alarm control signals.
Figure 8:
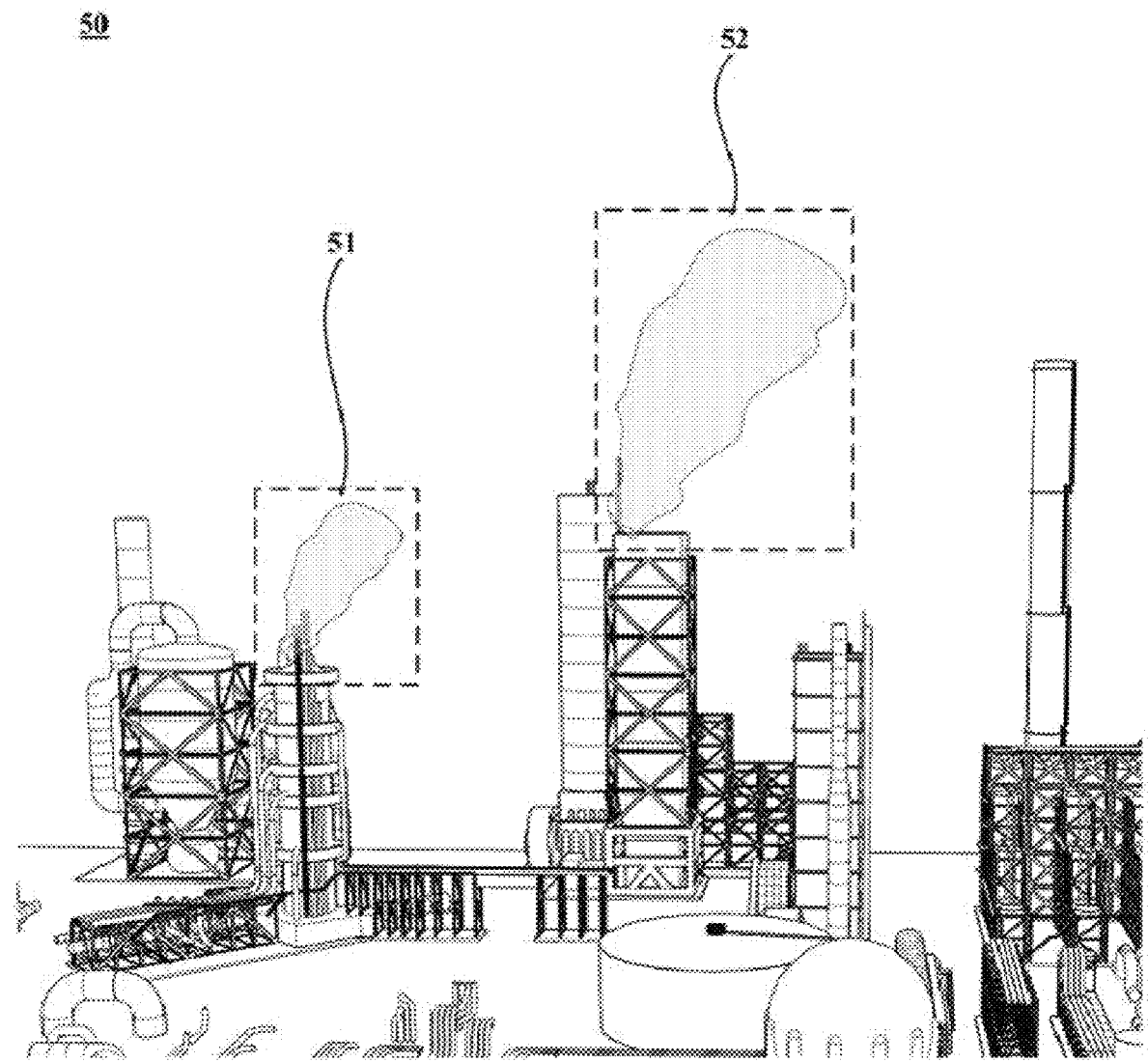
FIG. 8 illustrates chemical material leakage areas specified by a camera according to an embodiment.

FIG. 6 illustrates a flowchart of a chemical material leakage alarm-providing method (S100) according to an embodiment. FIG. 7 illustrates an alarm data set 40 in which various chemical material leakage states stored in the memory 102 are matched with various alarm control signals. FIG. 8 illustrates chemical material leakage areas specified by the image camera 140 according to an embodiment.

Referring to FIG. 6, the chemical material leakage alarm-providing method S100 according to an embodiment may provide a chemical material leakage alarm using the chemical material leakage-monitoring system 1 including the chemical material leakage alarm-providing system 30.

The chemical material leakage alarm-providing method S100 may include a step S110 of sensing external environmental information, a step (S120) of obtaining chemical material data, a step (S130) of predicting the diffusion pattern of a chemical material, a step (S140) of detecting chemical material information and a step (S150) of providing a user alert.

In the step S110 of sensing external environmental information, the controller 100 may sense external environmental information on the chemical material leakage alarm-providing system 30 using the environmental information-collecting sensor 120. Here, the environmental information may include information related to at least one of wind speed, wind direction, and temperature sensed using the environmental information-collecting sensor 120.

In the step (S120) of obtaining chemical material data, the controller 100 may obtain chemical material data using the chemical material-detecting device 110. The chemical material-detecting device 110 may obtain data on a chemical material leaked from a monitoring area at a location separated from the monitoring area.

Meanwhile, referring to FIG. 8, the processor 101 may specify a leakage area 51 or 52 of a chemical material by analyzing an image 50 of a monitoring area captured by the image camera 140, in the step (S120) of obtaining chemical material data.

For example, the processor 101 may specify the leakage area 51 of the first chemical material and the leakage area 52 of the second chemical material using an artificial neural network based on the image 50 of the monitoring area. Here, each of the leakage area 51 of the first chemical material and the leakage area 52 of the second chemical material may be an area including an outlet where each of the chemical materials is discharged.

The processor 101 may control the position of the chemical material-detecting device 110 such that the chemical material-detecting device 110 faces the leakage area 51 of the first chemical material and the leakage area 52 of the second chemical material. Accordingly, chemical material data acquisition for the area where the chemical material is leaked may be performed more precisely.

In the step (S130) of predicting the diffusion pattern of a chemical material, the processor 101 may predict the diffusion pattern of the chemical material leaked within the monitoring area based on the environmental information.

In detail, the processor 101 may calculate the diffusion pattern of the chemical material using information about at least one of wind speed, wind direction, and temperature. In addition, the processor 101 may calculate the coordinates of an expected leakage point of the chemical material by tracing back the diffusion pattern of the chemical material.

In this case, the processor 101 may calculate the diffusion pattern of the chemical material and the coordinates of the expected leakage point using an artificial neural network (ANN).

Here, the artificial neural network (ANN) may include a Deep Neural Network (DNN), a Convolutional Neural Network (CNN), a Recurrent Neural Network (RNN), or a Generative Adversarial Network (GAN), and may be implemented within the processor 101, or may be implemented as a separate processor outside the processor 101.

In the step (S140) of detecting chemical material information, the processor 101 may detect chemical material information based on chemical material data. For example, the chemical material information may be information on at least one of the type and concentration of the chemical material.

In the step (S150) of providing a user alert, the processor 101 may provide a user alert based on at least one of the diffusion pattern of a chemical material and chemical material information.

In detail, the processor 101 may generate various alarm control signals according to the alarm data set 40 in which various chemical material leakage states set based on at least one of the diffusion pattern of the chemical material and the material information are matched with various alarm control signals.

The alarm control signals generated by the processor 101 may be transmitted to the alarm device 130 through the communication part 104. Accordingly, the alarm device 130 may provide various types of user alarms.

Referring to FIG. 7, in the case of a first state in which a leakage-allowed chemical material included in a leakage-allowed chemical material list that has been preset and stored in the memory 102 is detected and the diffusion pattern of the leakage-allowed chemical material is determined to exceed a reference diffusion pattern range, the processor 101 may generate a first alarm control signal.

In addition, in the case of a second state in which a leakage-inhibited chemical material, which is not included in the leakage-allowed chemical material list, is detected, and the diffusion pattern of the leakage-inhibited chemical material is within a reference diffusion pattern range, the processor 101 may generate a second alarm control signal.

Here, the diffusion pattern range may include at least one of the diffusion speed and diffusion range of a chemical material.

Furthermore, in the case of a third state in which a leakage-inhibited chemical material not included in the leakage-allowed chemical material list is detected and the diffusion pattern of the leakage-inhibited chemical material exceeds a reference diffusion pattern range, the processor 101 may generate a third alarm control signal.

By providing different user alerts according to the leakage status of different chemical materials in such a manner, the user may quickly recognize various situations and take appropriate countermeasures accordingly, thereby preventing the expansion of accidents caused by chemical materials harmful to the human body.

Figure 9:
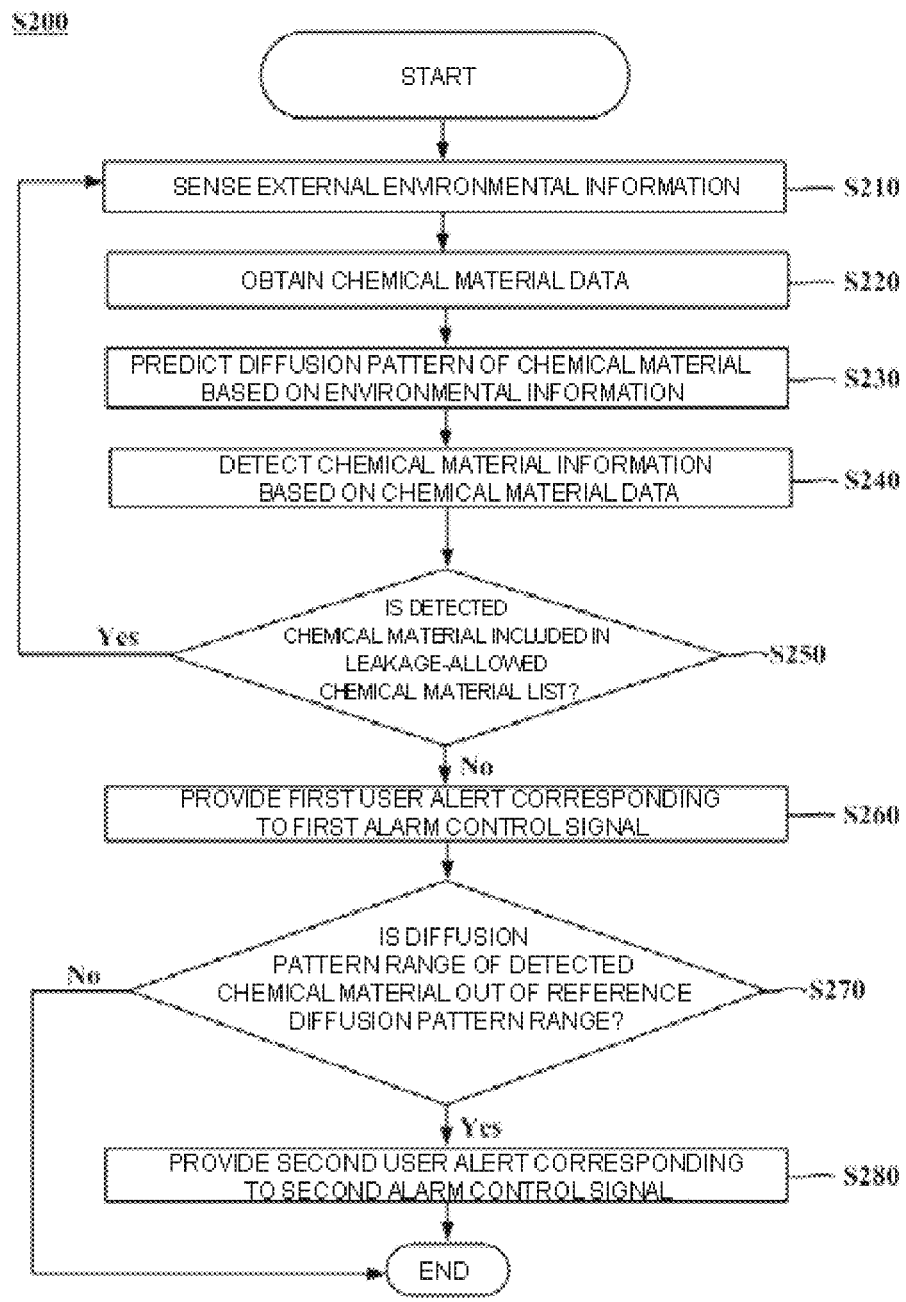
FIG. 9 illustrates a flowchart of a chemical material leakage alarm-providing method according to another embodiment.

FIG. 9 illustrates a flowchart of a chemical material leakage alarm-providing method S200 according to another embodiment.

Steps (S210), (S220), (S230) and (S240) of the chemical material leakage alarm-providing method S200 of FIG. 9 may be substantially the same as steps (S110), (S120), (S130) and (S140) of the chemical material leakage alarm-providing method S100 of FIG. 6.

Figure 10:
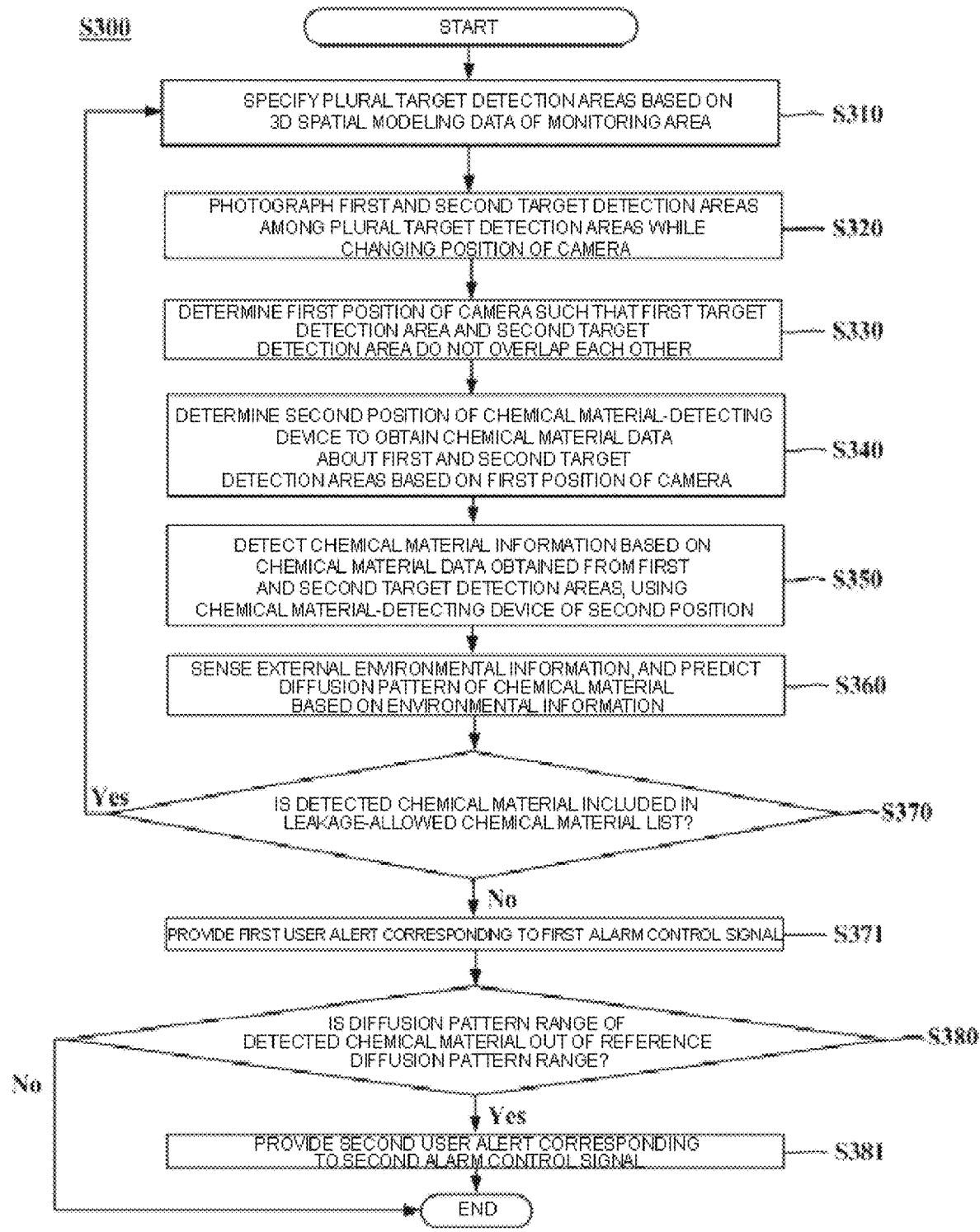
FIG. 10 illustrates a flowchart of a chemical material leakage alarm-providing method according to still another embodiment.

In the description of FIG. 9, contents overlapping with those of FIG. 10 are omitted.

Referring to FIG. 9, the chemical material leakage alarm-providing method S200 may include a step (S210) of sensing external environmental information, a step (S220) of obtaining chemical material data, a step (S230) of predicting the diffusion pattern of a chemical material, a step (S240) of detecting chemical material information, a step (S250) of determining whether the detected chemical material is included in the leakage-allowed chemical material list, a step (S260) of providing the first user alert, a step (S270) of determining whether the diffusion pattern range of the detected chemical material is outside a reference diffusion pattern range and a step (S280) of providing the second user alert.

In the step (S250) of determining whether the detected chemical material is included in the leakage-allowed chemical material list, the processor 101 may determine whether the detected chemical material is included in a leakage-allowed chemical material list that has been preset and stored in the memory 102. The chemical materials included in the leakage-allowed chemical material list may be materials that are usually leaked from the relevant industrial site and harmful to the human body.

When the detected chemical material is determined to be included in the leakage-allowed chemical material list, the processor 101 may return to step (S210).

When the detected chemical material is determined not to be included in the leakage-allowed chemical material list, the processor 101 may perform step (S250).

In the step (S260) of providing the first user alert, the processor 101 may generate the first alarm control signal corresponding to a state in which a chemical material not included in the leakage-allowed chemical material list is detected.

The first alarm control signal may be transmitted to the alarm device 130. Accordingly, the alarm device 130 may provide the first user alert corresponding to the first alarm control signal.

For example, the first user alert may include at least one of the alarm sound of the first pattern and the alarm light of the first color.

In the step (S270) of determining whether the diffusion pattern range of the detected chemical material is outside a reference diffusion pattern range, the processor 101 may determine whether the diffusion range of the diffusion pattern of the chemical material that is not included in the leakage-allowed chemical material list is outside the preset reference diffusion pattern range.

Here, the diffusion pattern range may include at least one of the diffusion speed and diffusion range of the chemical material.

For example, it may be determined whether the diffusion speed and diffusion range of the chemical material calculated based on the diffusion pattern of the chemical material predicted in step (S230) are outside the reference diffusion pattern range preset and stored in the memory 102. The reference diffusion pattern range may be preset by a user, or may be updated in real-time by a server 10 or the computing device 20.

When it is determined that the diffusion pattern range of the chemical material not included in the leakage-allowed chemical material list does not exceed the preset reference diffusion pattern range, the processor 101 may terminate the execution of the chemical material leakage alarm-providing method.

When it is determined that the diffusion pattern range of the chemical material not included in the leakage-allowed chemical material list is outside the preset reference diffusion pattern range, the processor 101 may perform step (S280).

In the step (S280) of providing the second user alert, the processor 101 may generate the second alarm control signal corresponding to the state in which the diffusion pattern range of the chemical material not included in the leakage-allowed chemical material list is outside the preset reference diffusion pattern range.

The second alarm control signal may be transmitted to the alarm device 130. Accordingly, the alarm device 130 may provide the second user alert corresponding to the second alarm control signal.

For example, the second user alert may include at least one of an alarm sound of the second pattern different from the first pattern and an alarm light of the second color different from the first color.

Figure 11:
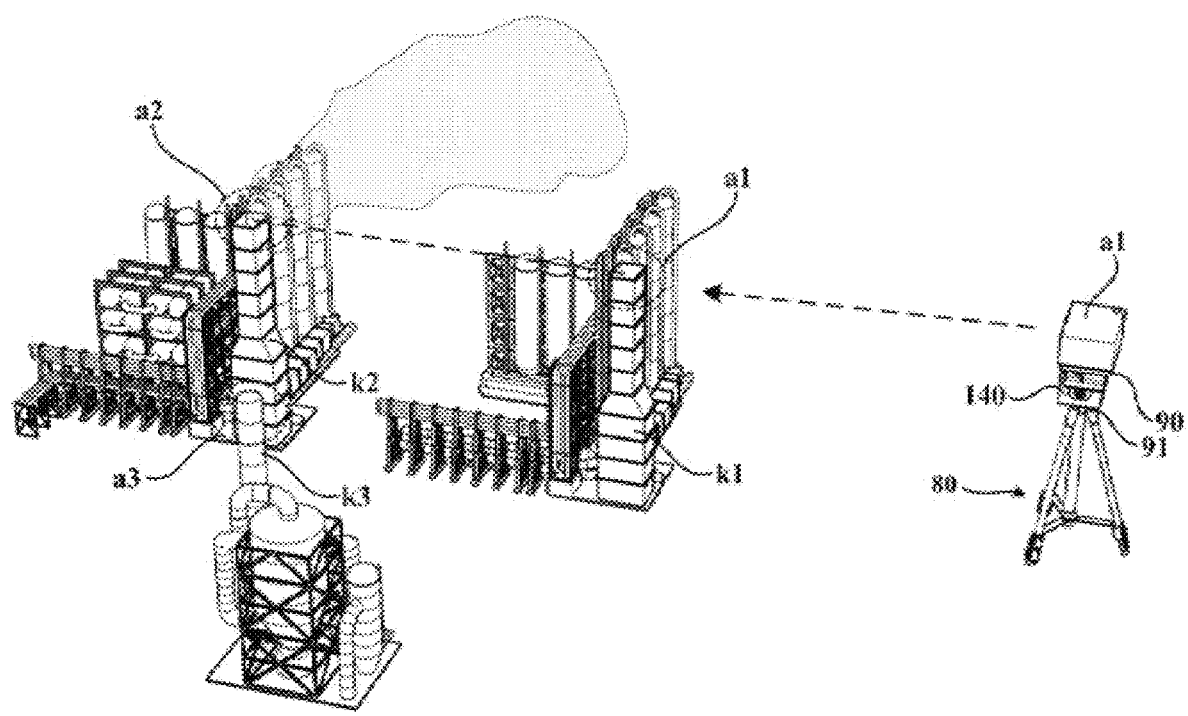
FIG. 11 is a drawing explaining a step of photographing a first target detection area and a second target detection area.
Figure 12:
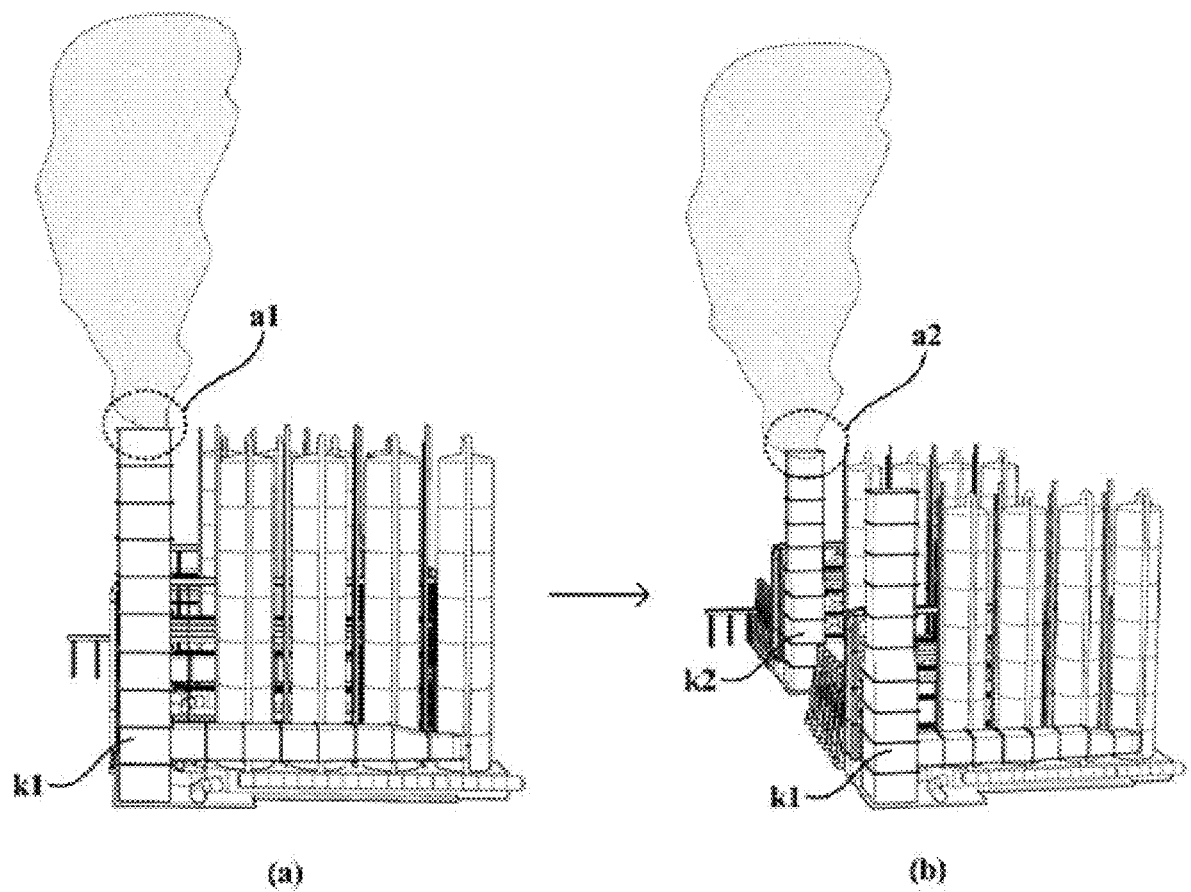
FIG. 12 is a drawing explaining a step of determining a first position of an image camera.

FIG. 10 illustrates a flowchart of a chemical material leakage alarm-providing method S300 according to still another embodiment. FIG. 11 is a drawing explaining a step of photographing a first target detection area a1 and a second target detection area a2. FIG. 12 is a drawing explaining a step of determining a first position of the image camera 140.

Steps (S370), (S371), (S380) and (S381) of FIG. 10 may be substantially the same as steps (S250), (S260), (S270) and (S280) of the chemical material leakage alarm-providing method S200 of FIG. 9, respectively.

In the description of FIG. 10, contents overlapping with those of FIG. 9 are omitted.

Referring to FIG. 10, the chemical material leakage alarm-providing method S300 may include a step (S310) of specifying a plurality of target detection areas, a step (S320) of photographing a first target detection area a1 and a second target detection area a2 among a plurality of target detection areas, a step (S330) of determining a first position of the image camera 140 that photographs the first target detection area a1 and the second target detection area a2 without overlapping each other, a step (S340) of determining a second position of the chemical material-detecting device 110, a step (S350) of detecting chemical material information on the first target detection area and the second target detection area, a step (S360) of predicting the diffusion pattern of the chemical material, a step (S370) of determining whether the detected chemical material is included in the leakage-allowed chemical material list, a step (S371) of providing the first user alert, a step (S380) of determining whether the diffusion pattern range of the detected chemical material is out of the reference diffusion pattern range and a step (S381) of providing a second user alert.

In the step (S310) of specifying a plurality of target detection areas, the processor 101 may specify a plurality of target detection areas based on the three-dimensional space modeling data of a monitoring area.

For example, referring to FIG. 11, the processor 101 may specify a plurality of target detection areas a1, a2 and a3, where a chemical material may be leaked using an artificial neural network, based on three-dimensional space modeling data for the monitoring area provided by the central server 10 or the computing device 20.

Here, a first target detection area a1 may be the entrance of a first outlet k1, a second target detection area a2 may be the entrance of a second outlet k2, and a third target detection area a3 5 may be the entrance of a third outlet k3.

In the step (S320) of photographing a first target detection area a1 and a second target detection area a2 among a plurality of target detection areas, the processor 101 may cause the image camera 140 to photograph the first target detection area a1 and the second target detection area a2. In this case, the processor 101 may control the operation of the second tilting part 91 so that the image camera 140 can photograph the first target detection area a1 and the second target detection area a2 in various positions.

In this case, as shown in FIG. 12(*a*), the image camera 140 may photograph an image of the first target detection area a1 and the second target detection area a2 overlapping each other. Accordingly, although the chemical material is actually discharged from the second outlet k2, the image camera 140 may photograph an image in which the chemical material appears to be discharged from the first outlet k1 located in front of the second outlet k2.

Accordingly, to obtain chemical material data for the first outlet k1, the processor 101 may control the position of the chemical material-detecting device 110 by controlling the operation of the first tilting part 90 such that the chemical material-detecting device 110 faces the first outlet k1.

In this case, chemical material detection is performed for the first outlet k1 where chemical material is not actually discharged, so that the accuracy of the alarm provision method based on chemical material information may be reduced.

In the step (S330) of determining a first position of the image camera 140 that photographs the first target detection area a1 and the second target detection area a2 without overlapping each other, the processor 101 may determine the first position of the image camera 140 allowing to photograph the first target detection area (a1) and the second target detection area (a2) without overlapping each other, during the process of photographing the monitoring area while changing the position of the image camera 140 in real-time.

For example, as shown in FIG. 12(*b*), the processor 101 may change the position of the image camera 140 in real-time such that the image camera 140 can capture an image in which the first target detection area a1 and the second target detection area a2 do not overlap each other.

In the step (S340) of determining a second position of the chemical material-detecting device 110, the processor 101 may determine the second position of the chemical material-detecting device 110 based on the first position of the image camera 140.

Here, the second position may be a position in which the chemical material-detecting device 110 actually faces the second target detection area a2 where the chemical material is leaked.

For example, the image camera 140 may analyze an image in which the first target detection area a1 and the second target detection area a2, which are photographed at the first position, do not overlap each other, and control the operation of the first tilting part 90 such that the chemical material-detecting device 110 faces the second target detection area a2, which is identified as the point where the chemical material is leaked, so that the position of the chemical material-detecting device 110 may be changed.

In the step (S350) of detecting chemical material information on the first target detection area a1 and the second target detection area a2, the processor 101 may operate the chemical material-detecting device 110 to obtain chemical material data for the first target detection area a1 and the second target detection area a2.

In the step (S360) of predicting the diffusion pattern of the chemical material, the processor 101 may sense external environmental information using the environmental information-collecting sensor 120 and predict the diffusion pattern of the chemical material based on the environmental information.

In this way, the processor 101 may detect a leaked chemical material in a state, where the first target detection area a1 and the second target detection area a2 among the plural target detection areas do not overlap each other, by changing the positions of the image camera 140 and the chemical material-detecting device 110, and may provide an appropriate user alert accordingly.

Figure 13:
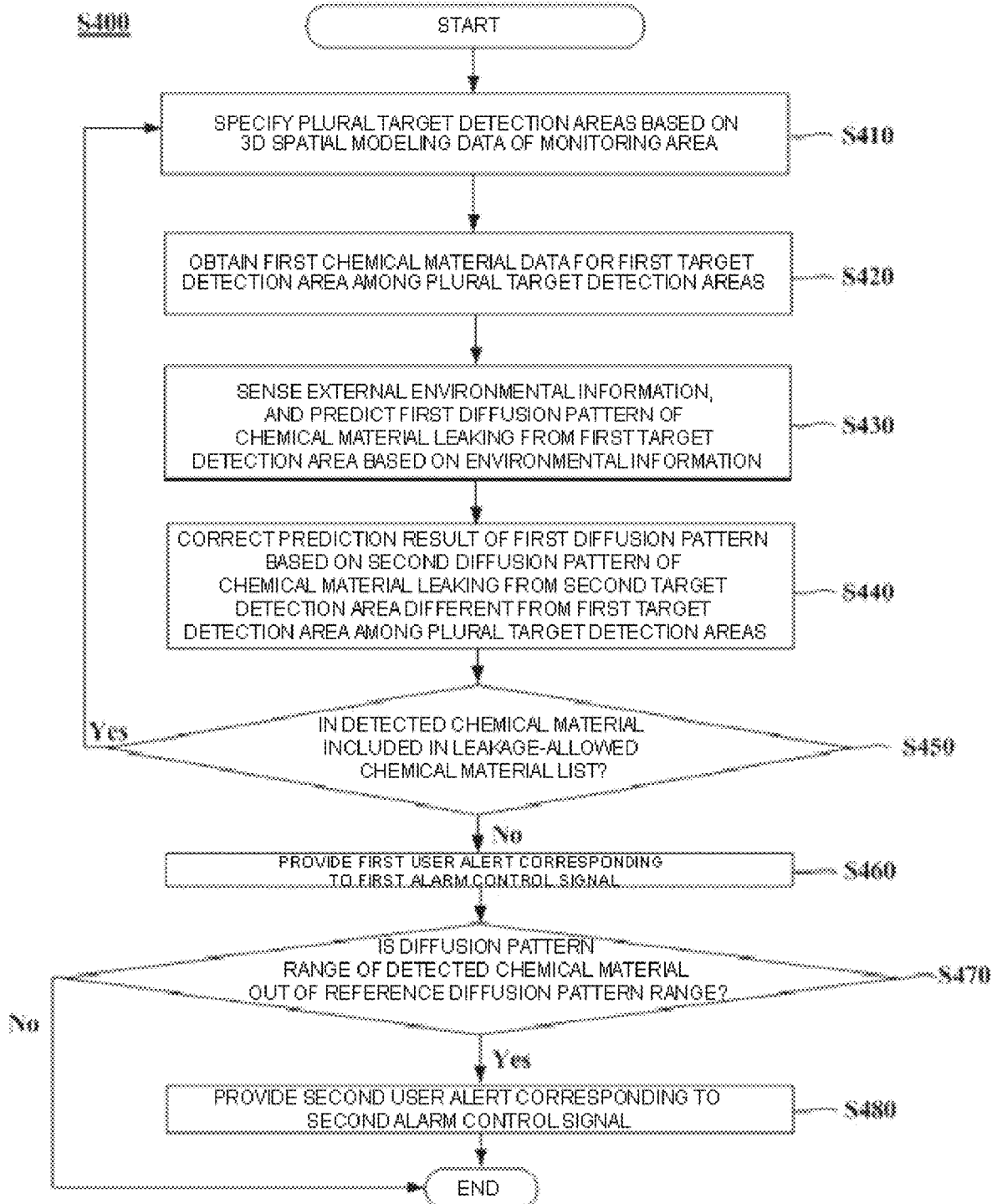
FIG. 13 illustrates a flowchart of a chemical material leakage alarm-providing method according to yet another embodiment.
Figure 14:
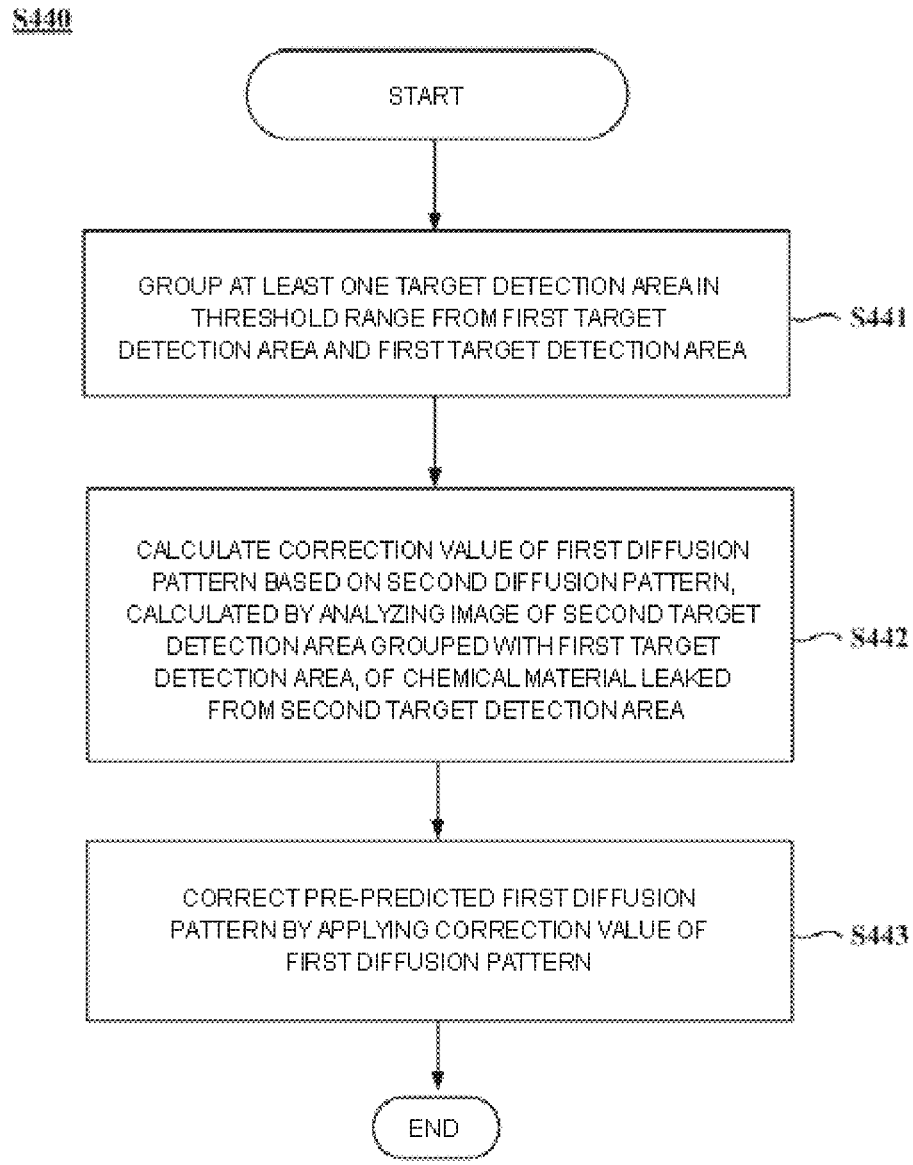
FIG. 14 is a flowchart for explaining a step of correcting the prediction result of the first diffusion pattern of FIG. 13.
Figure 15:
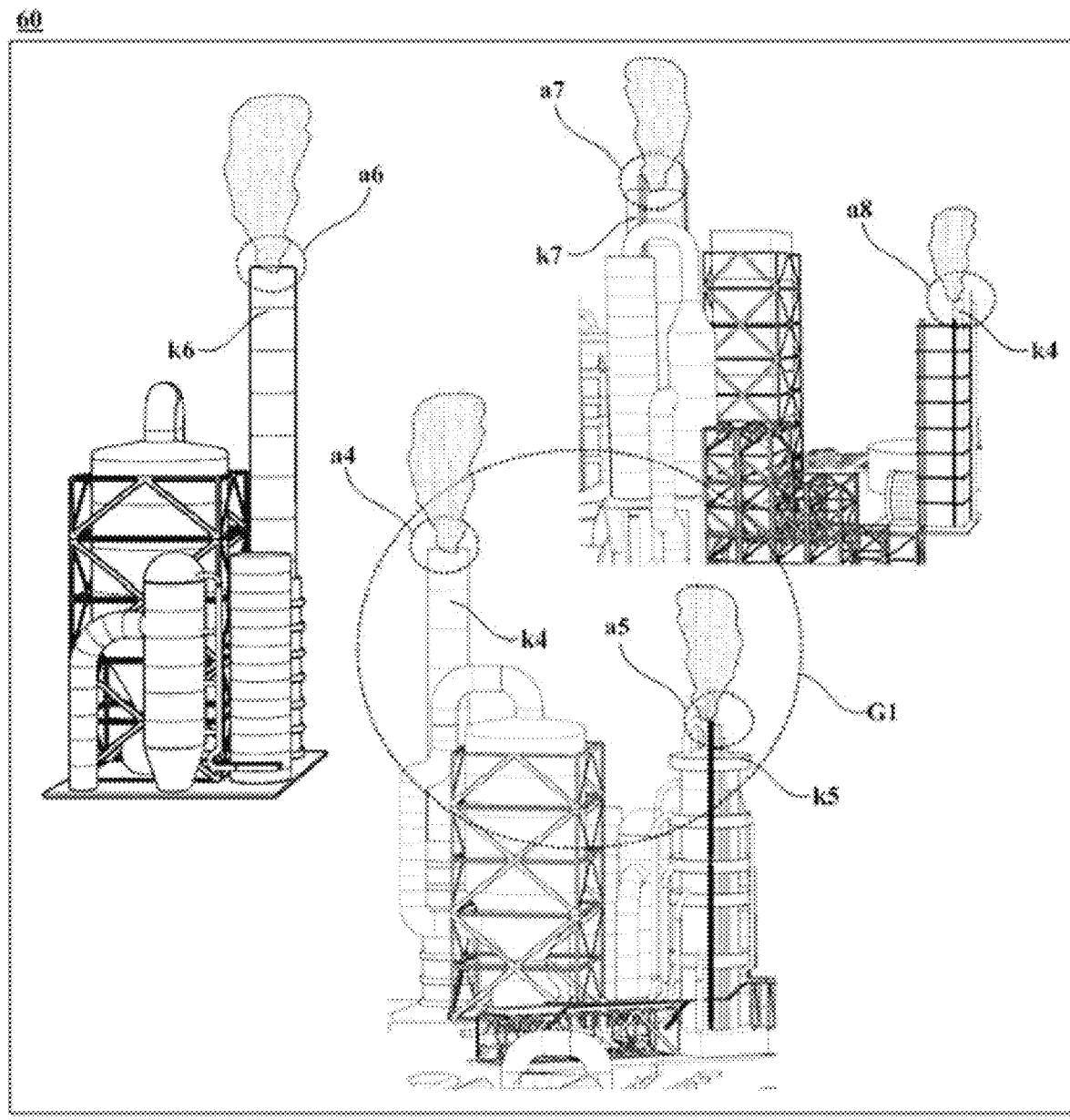
FIG. 15 is a drawing explaining a step of correcting the prediction result of the first diffusion pattern of FIG. 14.

FIG. 13 illustrates a flowchart of a chemical material leakage alarm-providing method S400 according to yet another embodiment. FIG. 14 is a flowchart for explaining a step (S440) of correcting the prediction result of the first diffusion pattern of FIG. 13. FIG. 15 is a drawing explaining a step (S440) of correcting the prediction result of the first diffusion pattern of FIG. 14.

Steps (S450), (S460), (S470) and (S480) of FIG. 13 may be substantially the same as steps (S250), (S260), (S270) and (S280) of the chemical material leakage alarm-providing method S200 of FIG. 9, respectively.

In the description of FIG. 13, contents overlapping with those of FIG. 9 are omitted.

Referring to FIG. 13, the chemical material leakage alarm-providing method S400 may include a step (S410) of specifying a plurality of target detection areas, a step (S420) of obtaining data of a first chemical material for the first target detection area a4, a step (S430) of predicting a first diffusion pattern of the chemical material leaked from the first target detection area a4, the step (S440) of correcting the prediction result of the first diffusion pattern, a step (S450) of determining whether the detected chemical material is included in the leakage-allowed chemical material list, a step (S460) of providing the first user alert, a step (S470) of determining whether the diffusion pattern range of the detected chemical material is out of the reference diffusion pattern range and a step (S480) of providing the second user alert.

In the step (S410) of specifying a plurality of target detection areas, the processor 101 may specify a plurality of target detection areas based on the three-dimensional space modeling data of a monitoring area.

For example, referring to FIG. 15, the processor 101 may specify a plurality of target detection areas a4, a5, a6, a7 and a8, where a chemical material may be leaked using an artificial neural network, based on three-dimensional space modeling data for the monitoring area provided by the central server 10 or the computing device 20.

Here, the first target detection area a4 may be the entrance of a first outlet k4, the second target detection area a5 may be the entrance of a second outlet k5, the third target detection area a6 may be the entrance of a third outlet k6, the fourth target detection area a7 may be the entrance of a fourth outlet k7, and the fifth target detection area a8 may be the entrance of a fifth outlet k8.

In the step (S420) of obtaining data of a first chemical material for the first target detection area a4, the processor 101 may control the chemical material-detecting device 110 to obtain chemical material data for the first target detection area a4 among the plural target detection areas a4, a5, a6, a7 and a8.

In the step (S430) of predicting a first diffusion pattern of the chemical material leaked from the first target detection area a4, the processor 101 may sense external environmental information by controlling the environmental information-collecting sensor 120, and may predict the first diffusion pattern of the chemical material leaked from the first target detection area a4 based on environmental information.

In this case, the external environmental information sensed through the environmental information-collecting sensor 120 is environmental information around the chemical material leakage alarm-providing system 30 located at a certain distance from the first target detection area a4, so the first diffusion pattern predicted based on this may be somewhat inaccurate.

In the step (S440) of correcting the prediction result of the first diffusion pattern, the processor 101 may correct the prediction result of the first diffusion pattern based on the second diffusion pattern of a chemical material leaking from a second target detection area different from the first target detection area.

In detail, referring to FIG. 14, the processor 101 may group the first target detection area (a4) with at least one other target detection area within a threshold range from the first target detection area a4 (S441), in the step (S440) of correcting the prediction result of the first diffusion pattern.

For example, the processor 101 may group the second target detection area a5 within a critical range from the first target detection area a4 and the first target detection area a4 into a first group G1. Here, the threshold range may be preset by the user or transmitted from the central server 10 or the computing device 20.

In addition, in the step (S440) of correcting the prediction result of the first diffusion pattern, the processor 101 may analyze the image of the second target detection area a5 photographed by the image camera 140 to calculate a second diffusion pattern of the chemical material leaking from the second target detection area a5. The processor 101 may calculate a correction value of the first diffusion pattern based on the second diffusion pattern (S442).

Furthermore, in the step (S440) of correcting the prediction result of the first diffusion pattern, the processor 101 may correct the predicted first diffusion pattern by applying the correction value of the first diffusion pattern.

By correcting the diffusion pattern of the detected chemical material in such a manner, the accuracy of the chemical material leakage alarm-providing method based on the corrected diffusion pattern may be improved.

The embodiments according to the present invention described above may be implemented in the form of program commands that can be executed through various computer components and recorded on a computer-readable recording medium. The computer-readable recording medium may include a program command, a data file, a data structure, etc. alone or in combination. The program instructions recorded on the computer-readable recording medium may be specially designed and configured for the present invention or may be known and available to those skilled in the art of computer software. Examples of computer-readable recording media include magnetic media such as hard disks, floppy disks and magnetic tapes, optical recording media such as CD-ROMs and DVDs, magneto-optical media such as floptical disks, and hardware devices, such as ROMs, RAMs, and flash memories, specifically configured to store and execute program instructions. Examples of program instructions include not only machine language codes such as those generated by a compiler, but also high-level language codes that can be executed by a computer using an interpreter, etc. Hardware devices may be modified with one or more software modules to perform processing according to the present invention, and vice versa.

The particular implementations shown and described herein are illustrative examples of the invention and are not intended to otherwise limit the scope of the invention in any way. For the sake of brevity, conventional electronics, control systems, software development and other functional aspects of the systems (and components of the individual operating components of the systems) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical".

In addition, although the detailed description of the present invention has been described with reference to preferred embodiments of the present invention, those skilled in the art or having common knowledge of the art will understand that the present invention can be modified and changed in various ways without departing from the idea and technical range of the present invention described in the accompanying claims. Therefore, the technical scope of the present invention should not be limited to the contents described in the detailed description of the specification, but should be defined by the scope of the accompanying claims.

INDUSTRIAL APPLICABILITY

The present invention has industrial applicability in that it can enhance the safety of industrial sites by efficiently sensing hazardous gases or hazardous chemical materials that may leak due to accidents in advanced industrial sites such as the semiconductor and display industries, which inevitably use a wide variety of hazardous gases such as acid gases of fluorine, chlorine, bromine, and nitric acid series and basic gases, e.g., ammonia and amines, and providing related alarms.

The invention claimed is:

1. A chemical material leakage alarm-providing method of detecting chemical material leakage in a monitoring area and providing a user alert, the chemical material leakage alarm-providing method comprising:
specifying a plurality of target detection areas based on three-dimensional space modeling data for the monitoring area;
photographing a first target detection area and a second target detection area among a plurality of target detection areas by controlling an image camera;
determining a first position of the image camera that captures images of the first target detection area and the second target detection area without overlapping each other;
specifying a point of chemical material leakage by the image camera analyzing an image in which the first target detection area and the second target detection area, captured at the first position, do not overlap;
determining a second position of a chemical material-detecting device so that the chemical material detection device is directed toward the second target detection area, which has been identified as the point where the chemical material is leaked among the first target detection area and the second target detection area;
sensing external environmental information using an environmental information-collecting sensor;
obtaining data about a chemical material on the second target detection area using the chemical material-detecting device;
predicting a diffusion pattern of the chemical material based on the environmental information;
detecting chemical material information based on the chemical material data; and
providing a user alert based on at least one of the diffusion pattern of the chemical material and the chemical material information.

2. The chemical material leakage alarm-providing method according to claim 1, wherein, in the providing, a user alert is provided to correspond to a leakage state determined according to at least one of the diffusion pattern of the chemical material and the chemical material information, and comprises at least one of an alarm sound, an alarm light and an alarm vibration.

3. The chemical material leakage alarm-providing method according to claim 1, wherein, in the detecting, chemical material information comprising at least one of a type and concentration of the chemical material is detected.

4. The chemical material leakage alarm-providing method according to claim 3, wherein, in the providing, a first user alert is provided when the detected chemical material is not comprised in a preset leakage-allowed chemical material list.

5. The chemical material leakage alarm-providing method according to claim 4, wherein, in the providing a user alert, a second user alert different from the first user alert is provided when a diffusion pattern range of the chemical material not comprised in the leakage-allowed chemical material list exceeds a preset reference diffusion pattern range.

6. The chemical material leakage alarm-providing method according to claim 5, wherein the first user alert comprises at least one of an alarm sound of a first pattern and an alarm light of a first color, and the second user alert comprises at least one of an alarm sound of a second pattern different from the first pattern and an alarm light of a second color different from the first color.

7. The chemical material leakage alarm-providing method according to claim 5, wherein the diffusion pattern range comprises at least one of a diffusion speed and diffusion range of a chemical material.

8. A chemical material leakage alarm-providing system installed at a location spaced apart from a monitoring area where a chemical material is leaked and configured to detect leakage of the chemical material and provide the leakage to a user alert, the chemical material leakage alarm-providing system comprising:
a chemical material-detecting device for obtaining data of the chemical material leaking from the monitoring area;
an environmental information-collecting sensor for sensing external environmental information;
a controller comprising a memory storing one or more programs comprising a command; and a processor executing the programs to predict a diffusion pattern of the chemical material based on the environmental information, detect chemical material information based on data about the chemical material, and generate an alarm control signal based on at least one of the diffusion pattern of the chemical material and the chemical material information;

an alarm device for providing a user alert corresponding to the alarm control signal transmitted from the controller; and an image camera for photographing an external object, wherein the processor specifies a plurality of target detection areas based on three-dimensional space modeling data for the monitoring area, and determines a position of the image camera such that two target detection areas among the plural target detection areas are photographed without overlapping each other.

9. The chemical material leakage alarm-providing system according to claim 8, wherein the user alert corresponds to a leakage state determined according to at least one of the diffusion pattern of the chemical material and the chemical material information, and comprises at least one of an alarm sound, an alarm light and an alarm vibration.

10. The chemical material leakage alarm-providing system according to claim 8, wherein the chemical material information comprises at least one of a type and concentration of the chemical material.

11. The chemical material leakage alarm-providing system according to claim 10, wherein the processor determines whether the detected chemical material is comprised in a leakage-allowed chemical material list stored in the memory, and, when the detected chemical material is not comprised in the leakage-allowed chemical material list, generates a first alarm control signal such that the alarm device provides a first user alert, and transmits it to the alarm device.

12. The chemical material leakage alarm-providing system according to claim 11, wherein, when a diffusion pattern range of the chemical material not comprised in the leakage-allowed chemical material list is outside a reference diffusion pattern range stored in the memory, the processor generates a second alarm control signal such that the alarm device provides a second user alert different from the first user alert, and transmits it to the alarm device.

13. The chemical material leakage alarm-providing system according to claim 12, wherein the first user alert comprises at least one of an alarm sound of a first pattern and an alarm light of a first color, and the second user alert comprises at least one of an alarm sound of a second pattern different from the first pattern and an alarm light of a second color different from the first color.

14. The chemical material leakage alarm-providing system according to claim 12, wherein the diffusion pattern range comprises at least one of a diffusion speed and diffusion range of a chemical material.

15. The chemical material leakage alarm-providing system according to claim 8, wherein the processor specifies a leakage area of the chemical material by analyzing an image of the monitoring area photographed by the image camera, and controls a position of the chemical material-detecting device such that the chemical material-detecting device faces the specified leakage area of the chemical material.

* * * * *